US012648697B2

(12) United States Patent
Yamamoto et al.

(10) Patent No.: US 12,648,697 B2
(45) Date of Patent: Jun. 9, 2026

(54) DETECTION APPARATUS AND MEASURING APPARATUS

(71) Applicant: SEIKO EPSON CORPORATION, Tokyo (JP)

(72) Inventors: Tetsuya Yamamoto, Suwa (JP); Takefumi Fukagawa, Suwa-gun (JP)

(73) Assignee: SEIKO EPSON CORPORATION, Tokyo (JP)

( * ) Notice: Subject to any disclaimer, the term of this patent is extended or adjusted under 35 U.S.C. 154(b) by 568 days.

(21) Appl. No.: 18/113,741

(22) Filed: Feb. 24, 2023

(65) Prior Publication Data
US 2023/0270331 A1 Aug. 31, 2023

(30) Foreign Application Priority Data
Feb. 25, 2022 (JP) ................................. 2022-027405

(51) Int. Cl.
A61B 5/00 (2006.01)
H10K 59/65 (2023.01)

(52) U.S. Cl.
CPC ........... A61B 5/0059 (2013.01); H10K 59/65 (2023.02)

(58) Field of Classification Search
CPC ............ A61B 5/0059; A61B 2562/185; A61B 5/0205; A61B 5/02444; A61B 5/0075; A61B 5/681; A61B 5/14551; A61B 5/7225; A61B 5/72; H10K 59/65
See application file for complete search history.

(56) References Cited

U.S. PATENT DOCUMENTS

| | | | |
|---|---|---|---|
| 8,552,378 B2 | 10/2013 | Kanda et al. | |
| 8,710,442 B2 | 4/2014 | Kanda et al. | |
| 2012/0256089 A1 | 10/2012 | Kanda et al. | |
| 2014/0070100 A1 | 3/2014 | Kanda et al. | |
| 2017/0251963 A1 | 9/2017 | Hashimoto et al. | |
| 2018/0070829 A1* | 3/2018 | Iwawaki | A61B 5/681 |
| 2018/0364095 A1* | 12/2018 | Nagaya | G01S 7/4816 |

FOREIGN PATENT DOCUMENTS

| | | |
|---|---|---|
| CN | 102727212 A | 10/2012 |
| CN | 107149478 A | 9/2017 |
| JP | 2016-158701 A | 9/2016 |
| JP | 2018-42597 A | 3/2018 |
| JP | 2018-149157 A | 9/2018 |
| JP | 2018/165639 A | 10/2018 |

* cited by examiner

*Primary Examiner* — Abid A Mustansir
(74) *Attorney, Agent, or Firm* — Oliff PLC

(57) ABSTRACT
A detection apparatus includes a semiconductor substrate, a first photoelectric conversion unit formed at the semiconductor substrate, a first light emitting layer formed by being stacked at the semiconductor substrate, and a first filter layer formed by being stacked at the first photoelectric conversion unit.

12 Claims, 7 Drawing Sheets

DETECTION APPARATUS AND MEASURING APPARATUS

The present application is based on, and claims priority from JP Application Serial Number 2022-027405, filed Feb. 25, 2022, the disclosure of which is hereby incorporated by reference herein in its entirety.

BACKGROUND

1. Technical Field

The present disclosure relates to a detection apparatus and a measuring apparatus including a light emitting unit and a light receiving unit.

2. Related Art

Various measurement technologies for non-invasively measuring biological information such as heartbeats have been proposed in the related art. JP 2018-149157 A and JP 2018-042597 A each describe a detection apparatus including a light emitting unit configured to emit light toward a living body, and a light receiving unit configured to receive light reflected by the living body. Biological information can be acquired by analyzing a signal output from the light receiving unit of this type of detection apparatus.

The detection apparatus (detection element) in JP 2018-149157 includes a substrate at which a light source (organic EL element or LED) as the light emitting unit is mounted. The substrate is mounted with a photodiode, a phototransistor, a photoconductive cell, an image sensor, or the like, as the light receiving unit, at a position adjacent to the light source.

The detection apparatus (optical sensor module) of JP 2018-042597 A uses a flexible printed circuit board as the substrate at which the light emitting unit and the light receiving unit are disposed. The light emitting unit is an LED, and the light receiving unit is a photodiode. By using the flexible printed circuit board, the substrate can be thinned, so that the detection apparatus can be thinned.

In the detection apparatus of each of JP 2018-149157 A and JP 2018-042597, each of the LED used as the light emitting unit and the photodiode used as the light receiving unit is chipped, and can be handled as a component. Therefore, when mounting on a surface of the substrate, it is necessary to provide a constant clearance between the light emitting unit and the light receiving unit in accordance with mounting accuracy of the chip. Thus, there is a limit for miniaturization of the detection apparatus.

SUMMARY

In order to solve the problem described above, a detection apparatus of the present disclosure includes a semiconductor substrate, a light emitting unit disposed at the semiconductor substrate, and configured to emit light toward a living body, and a light receiving unit disposed at the semiconductor substrate, and configured to receive the light from the living body, wherein the light receiving unit includes a first photoelectric conversion unit for receiving the light, and a first filter layer for limiting an incident angle of the light incident on the first photoelectric conversion unit.

A measuring apparatus of the present disclosure includes the detection apparatus described above, and an information analysis unit configured to identify biological information from a detection signal indicating a detection result of the detection apparatus.

DESCRIPTION OF EXEMPLARY EMBODIMENTS

Figure 1:
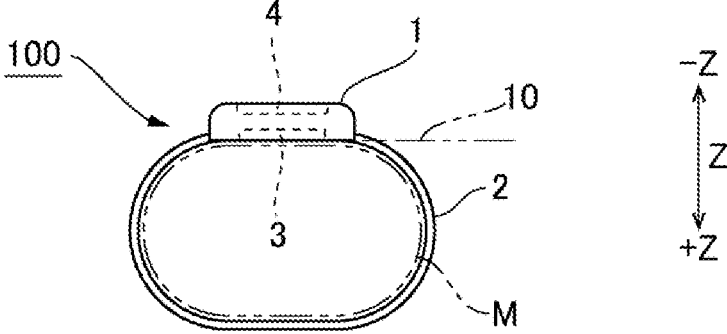
FIG. 1 is a side view of a measuring apparatus to which the present disclosure is applied.

Exemplary embodiments of the present disclosure are described below with reference to the accompanying drawings. Note that in each of the drawings, each member is schematically illustrated in a size to be recognizable, and actual dimensions and ratios may be different from those illustrated in the drawings.

Measuring Apparatus

FIG. 1 is a side view of a measuring apparatus 100 to which the present disclosure is applied. The measuring apparatus 100 is a biometric measuring apparatus for non-invasively measuring biological information. The measuring apparatus 100 is used facing a site to be measured (hereinafter referred to as a "measuring site M") in a subject's body (living body). In the example illustrated in FIG. 1, the measuring apparatus 100 is a wristwatch type portable device including a housing 1 and a belt 2. The measuring site M is a wrist of the subject. The measuring apparatus 100 is worn and used by winding the band-shaped belt 2 around the wrist of the subject, so that a detection surface 10 of the housing 1 faces a skin surface of the wrist (measuring site M).

In the present specification, an X direction, a Y direction, and a Z direction are directions orthogonal to each other. The Z direction is a normal direction of the detection surface 10. A +Z direction is a direction from the detection surface 10 toward the measuring site M, and a −Z direction is a direction from the measuring site M toward the detection surface 10.

In the present specification, a heartbeat (for example, a pulse rate) and an oxygen saturation ($SpO_2$) of the subject are exemplified as biological information. The heartbeat indicates the change of the internal volume of a blood vessel over time due to the pulsation of the heart. The oxygen saturation indicates the proportion (%) of hemoglobin bound to oxygen in hemoglobin in the blood of the subject and is an index for evaluating the respiratory function of the subject.

Figure 2:
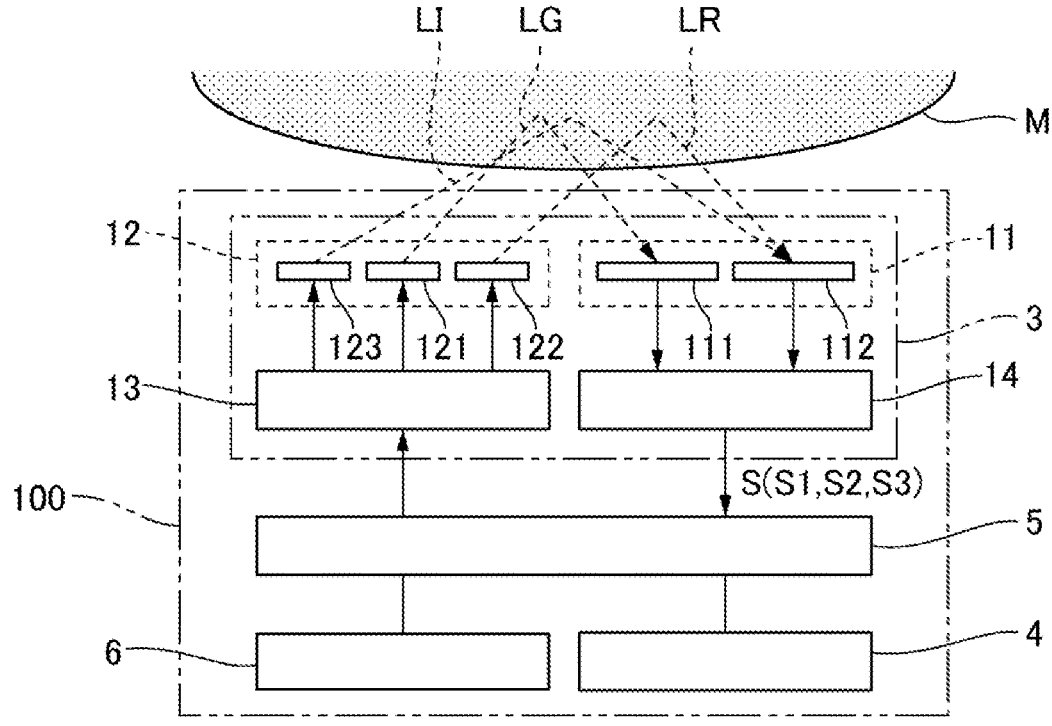
FIG. 2 is a block diagram illustrating a functional configuration of the measuring apparatus to which the present disclosure is applied.

FIG. 2 is a block diagram illustrating a functional configuration of the measuring apparatus 100 to which the present disclosure is applied. As illustrated in FIG. 2, the measuring apparatus 100 includes a control device 5, a storage device 6, a display device 4, and a detection apparatus 3. The control device 5 and the storage device 6 are disposed inside the housing 1. The detection apparatus 3 is disposed at the detection surface 10. The display device 4 is disposed at a surface of the housing 1 on an opposite side to the detection surface 10. The display device 4 displays various images including measurement results under control of the control device 5. The display device 4 is, for example, a liquid crystal display panel.

Note that, in addition to the functional configuration illustrated in FIG. 2, the measuring apparatus 100 may be configured to include an operation unit such as an operation button or a touch panel disposed at the surface of the housing 1, and to input an operation signal in accordance with an operation for the operation unit to the control device 5. Furthermore, a communication unit configured to output a measurement result to an outside and input a signal from the outside to the control device 5 may be included. Alternatively, a voice output unit or a vibration unit may be included as a device for notifying of a measurement result.

As illustrated in FIG. 2, the detection apparatus 3 includes a light receiving unit 11, a light emitting unit 12, a drive circuit 13, and an output circuit 14. One or both of the drive circuit 13 and the output circuit 14 can also be installed as circuits external to the detection apparatus 3. That is, the drive circuit 13 and the output circuit 14 may be omitted from the detection apparatus 3.

The detection apparatus 3 is a reflective optical sensor module that emits light from the detection surface 10, receives light incident on the detection surface 10 from the measuring site M, and generates detection signals S. That is, in the detection apparatus 3 of the present exemplary embodiment, the light receiving unit 11 and the light emitting unit 12 are disposed at the detection surface 10. The light emitting unit 12 includes a first light emitting element 121, a second light emitting element 122, and a third light emitting element 123. The first light emitting element 121, the second light emitting element 122, and the third light emitting element 123 emit light having different wavelengths from the detection surface 10, respectively.

The first light emitting element 121 emits first light LG. The first light LG is, for example, green light having a green wavelength band from 520 nm to 550 nm, and is light having a peak wavelength of 520 nm. The second light emitting element 122 emits second light LR. The second light LR is, for example, red light having a red wavelength band from 600 nm to 800 nm, and is light having a peak wavelength of 660 nm. The third light emitting element 123 emits third light LI. The third light is, for example, near-infrared light having a near-infrared wavelength band from 800 nm to 1300 nm. The third light LI is, for example, light having a peak wavelength of 905 nm. Note that, the wavelengths of light emitted by the respective light emitting elements are not limited to the above wavelength bands.

The drive circuit 13 supplies a drive current to cause each of the first light emitting element 121, the second light emitting element 122, and the third light emitting element 123 to emit light. For example, the drive circuit 13 periodically causes each of the first light emitting element 121, the second light emitting element 122, and the third light emitting element 123 to emit light in a time-division manner. The light emitted from each of the first light emitting element 121, the second light emitting element 122, and the third light emitting element 123 is incident on the measuring site M from the detection surface 10, propagates while repeatedly reflecting and scattering inside the measuring site M, then is emitted from the measuring site M, and is incident on the light receiving unit 11 disposed at the detection surface 10.

The light receiving unit 11 includes a first light receiving unit 111 and a second light receiving unit 112. Each of the first light receiving unit 111 and the second light receiving unit 112 generates a detection signal according to intensity of received light.

The first light receiving unit 111 receives the first light LG that has propagated in the measuring site M after being emitted from the first light emitting element 121 and generates a detection signal according to intensity of the received light. The second light receiving unit 112 receives the second light LR that has propagated in the measuring site M after being emitted from the second light emitting element 122 or the third light LI that has propagated in the measuring site M after being emitted from the third light emitting element 123 and generates detection signals according to intensity of the received light.

The output circuit 14 is configured to include, for example, an A/D converter that converts detection signals generated by each of the first light receiving unit 111 and the second light receiving unit 112 from analog to digital and an amplifier circuit that amplifies the converted detection signals (both not illustrated) and generates the plurality of detection signals S (S1, S2, S3) corresponding to wavelengths different from each other.

The detection signal S1 is a signal indicating the intensity of light received by the first light receiving unit 111 when it has received the first light LG (green light) emitted from the first light emitting element 121. The detection signal S2 is a signal indicating the intensity of light received by the second light receiving unit 112 when it has received the second light LR (infrared light) emitted from the second light emitting element 122. The detection signal S3 is a signal indicating the intensity of light received by the second light receiving unit 112 when it has received the third light LI (near-infrared light) emitted from the third light emitting element 123.

Each detection signal S is a heartbeat signal including periodic fluctuations corresponding to pulsations (volume heartbeats) of the artery inside the measuring site M because the amounts of absorption by blood during dilation and contraction of blood vessels generally differ.

The drive circuit 13 and the output circuit 14 are each mounted at a substrate in a form of an IC chip, for example. As described below, in the present exemplary embodiment, the light receiving unit 11 and the light emitting unit 12 are formed at the same semiconductor substrate 20 (see FIGS. 3 and 4). The drive circuit 13 and the output circuit 14 are mounted at a circuit disposition portion of the semiconductor substrate 20 at which the light receiving unit 11 and the light emitting unit 12 are formed. Note that the drive circuit 13 and the output circuit 14 may be mounted at a substrate that is separate from the semiconductor substrate 20 at which the light receiving unit 11 and the light emitting unit 12 are formed. Alternatively, the drive circuit 13 and the output circuit 14 can be installed as external circuits of the detection apparatus 3 as described above.

The control device 5 is an arithmetic processing unit such as a central processing unit (CPU) or a field-programmable gate array (FPGA) and controls the entirety of the measuring apparatus 100. The storage device 6 includes, for example, a non-volatile semiconductor memory and stores a program executed by the control device 5 and various data used by the control device 5. Note that, a configuration may be adopted in which the functions of the control device 5 are distributed over a plurality of integrated circuits or a configuration in which some or all of the functions of the control device 5 are realized by a dedicated electronic circuit. Note that, although the control device 5 and the storage device 6 are illustrated as separate elements in FIG. 2, the control device 5 including the storage device 6 can also be realized, for example, by an ASIC, or the like.

The control device 5 identifies biological information of the subject from the plurality of detection signals S (S1, S2, S3) generated by the detection apparatus 3 by executing the program stored in the storage device 6. Specifically, the control device 5 can identify a heartbeat of the subject from the detection signal S1 indicating the intensity of first light LG (green light) received by the first light receiving unit 111. The control device 5 can identify a pulse rate of the subject based on, for example, the detection signal S1. Further, the control device 5 can also identify the oxygen saturation (SpO$_2$) of the subject by analyzing the detection signal S2 indicating the intensity of second light LR (red light) received by the light receiving unit 11, and the detection signal S3 indicating the intensity of third light LI (near-infrared light) received by the light receiving unit 11.

The control device 5 functions as an information analysis unit that identifies the biological information from the detection signals S indicating the detection results of the detection apparatus 3 as described above. The control device (information analysis unit) 5 causes the display device 4 to display the biological information identified from the detection signals S. It is also possible to notify the user of the measurement result by voice output. It is also possible to notify the user of a warning (possibility of impaired physical function) when the pulse rate or oxygen saturation has fluctuated to values out of a predetermined range.

Detailed Configuration of Light Emitting Unit and Light Receiving Unit

Figure 3:
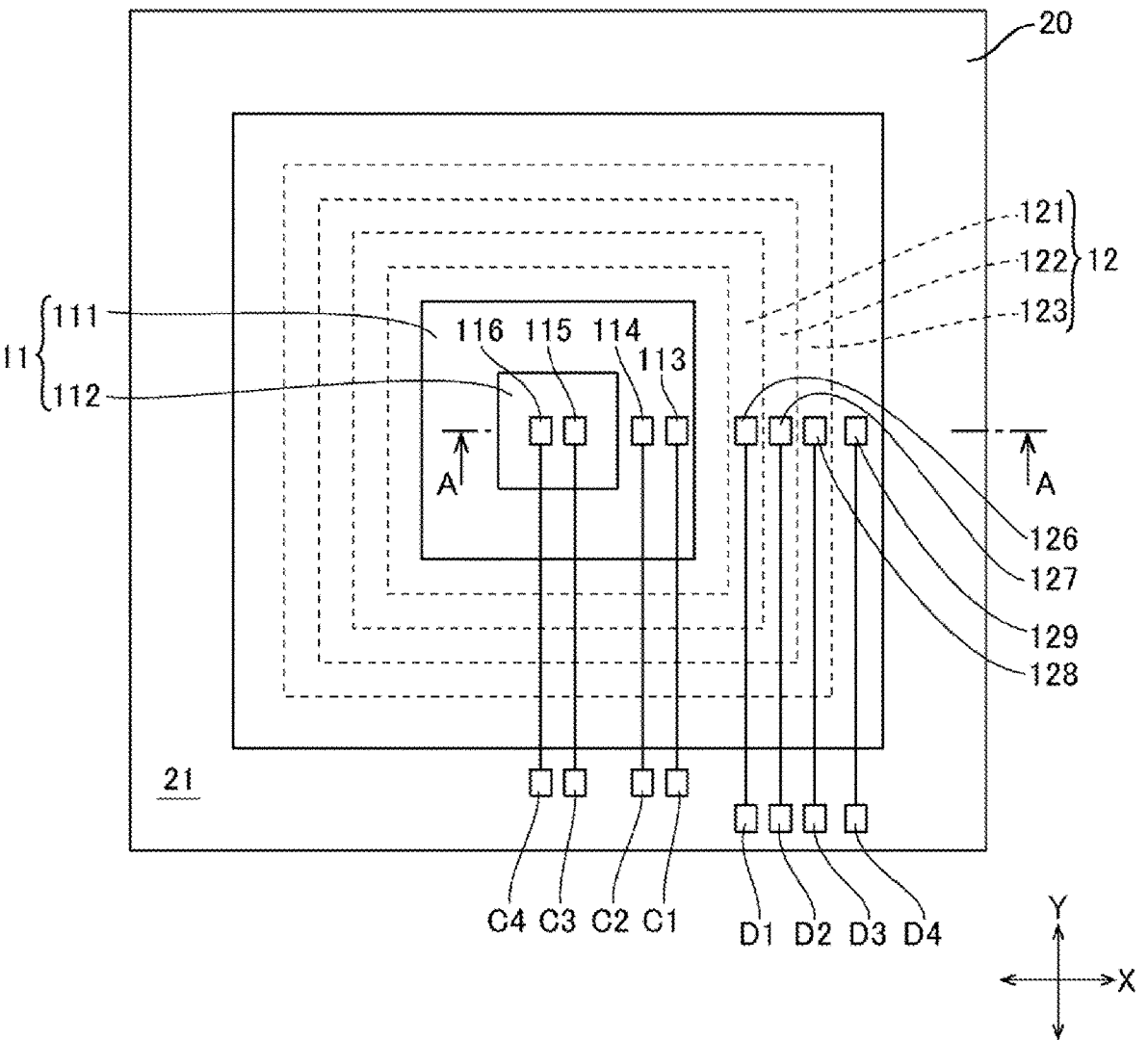
FIG. 3 is a plan view schematically illustrating planar shapes of a light receiving unit and a light emitting unit.
Figure 4:
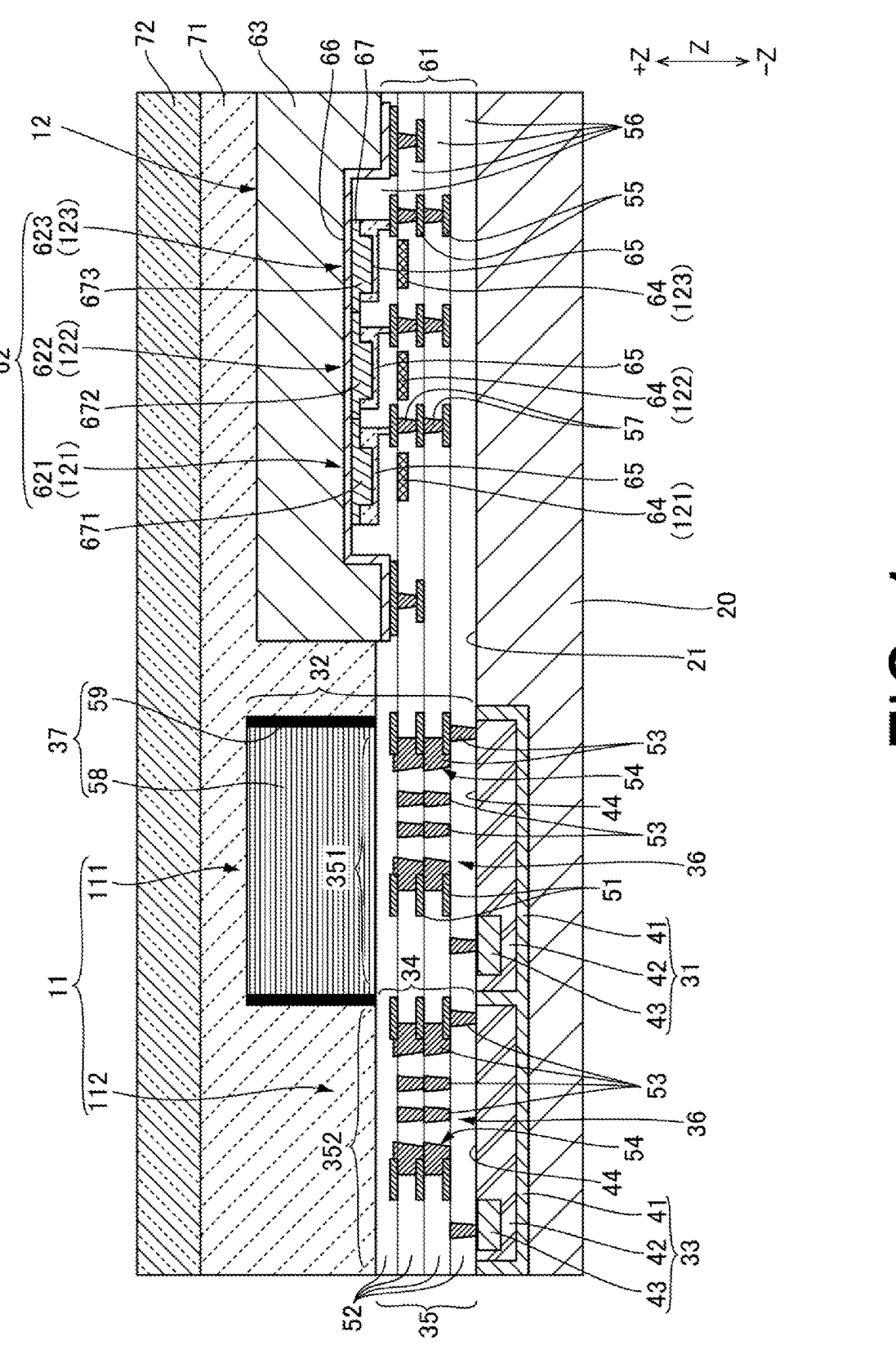
FIG. 4 is a cross-sectional view schematically illustrating a cross-sectional configuration of the light receiving unit and the light emitting unit.

FIG. 3 is a plan view schematically illustrating planar shapes of the light receiving unit 11 and the light emitting unit 12. FIG. 4 is a cross-sectional view schematically illustrating a cross-sectional configuration of the light receiving unit 11 and the light emitting unit 12 of FIG. 3, illustrating a cross-sectional configuration cut at a position A-A in FIG. 3. In the present exemplary embodiment, the light receiving unit 11 and the light emitting unit 12 are formed at the same semiconductor substrate 20. The semiconductor substrate 20 is formed of a semiconductor material such as silicon (Si), for example, and is utilized as a base (foundation) at which the light receiving unit 11 and the light emitting unit 12 are formed. As illustrated in FIG. 4, the light receiving unit 11 and the light emitting unit 12 are formed at a first surface 21 of the semiconductor substrate 20. The first surface 21 is a surface facing the +Z direction. The light receiving unit 11 and the light emitting unit 12 are formed at positions adjacent to each other at the first surface 21.

As described above, the light receiving unit 11 includes the first light receiving unit 111 and the second light receiving unit 112. As illustrated in FIG. 4, the first light receiving unit 111 is formed at a position adjacent to the light emitting unit 12. The second light receiving unit 112 is disposed on a side opposite to the light emitting unit 12 with respect to the first light receiving unit 111. Accordingly, the second light receiving unit 112 is farther away from the light emitting unit 12 than the first light receiving unit 111.

As illustrated in FIG. 3, in the present exemplary embodiment, the light receiving unit 11 is rectangular. In the light receiving unit 11, the second light receiving unit 112 is centrally disposed, and the first light receiving unit 111 has a shape surrounding an outer periphery of the second light receiving unit 112 in a belt shape with a constant width. The light receiving unit 11 includes an anode electrode 113 and a cathode electrode 114 corresponding to the first light receiving unit 111, and an anode electrode 115 and a cathode electrode 116 corresponding to the second light receiving unit 112. These electrodes are electrically coupled to terminals C1, C2, C3, and C4 disposed outside the light receiving unit 11 and the light emitting unit 12, respectively, via wiring formed in an angle limiting filter layer 35, which will be described later.

The light emitting unit 12 has a shape surrounding an outer periphery of the light receiving unit 11. The first light emitting element 121 that emits the first light LG (green light) is disposed in an inner peripheral region of the light emitting unit 12, and surrounds the outer periphery of the light receiving unit 11 in a belt shape with a constant width. The second light emitting element 122 that emits the second light LR (red light) surrounds an outer periphery of the first light emitting element 121 in a belt shape with a constant width. The third light emitting element 123 that emits the third light LI (near-infrared light) is disposed in an outer peripheral region of the light emitting unit 12, and surrounds an outer periphery of the second light emitting element 122 in a belt shape with a constant width. Accordingly, the second light emitting element 122 is farther away from the light receiving unit 11 than the first light emitting element 121. The third light emitting element 123 is farther away from the light receiving unit 11 than the second light emitting element 122.

The light emitting unit 12 includes anode contacts 126, 127, and 128 corresponding to the first light emitting element 121, the second light emitting element 122, and the third light emitting element 123, respectively, and a common cathode contact 129. The anode contacts 126, 127, 128 and the cathode contact 129 are electrically coupled to terminals D1, D2, D3, and D4 disposed outside the light receiving unit 11 and the light emitting unit 12, respectively, via wiring formed in a wiring layer 61 described later.

Cross-Sectional Configuration of Light Receiving Unit

As illustrated in FIG. 4, the first light receiving unit 111 includes a first photoelectric conversion unit 31 formed in a layer of the semiconductor substrate 20, and a first filter 32 formed by being stacked on a surface in the +Z direction of the first photoelectric conversion unit 31. The second light receiving unit 112 includes a second photoelectric conversion unit 33 formed at a position adjacent to the first photoelectric conversion unit 31 in the layer of the semiconductor substrate 20, and a second filter layer 34 formed by being stacked at a surface of the second photoelectric conversion unit 33. The second photoelectric conversion unit 33 is farther away from the light emitting unit 12 than the first photoelectric conversion unit 31.

Each of the first photoelectric conversion unit 31 and the second photoelectric conversion unit 33 includes a photodiode, such as a PIN type photodiode or a PN type photodiode, or a phototransistor. In the example illustrated in FIG. 4, each of the first photoelectric conversion unit 31 and the second photoelectric conversion unit 33 includes an n-type semiconductor layer 41 embedded in the semiconductor substrate 20, a p-type semiconductor layer 42 formed inside the n-type semiconductor layer 41, and an n-type semiconductor layer 43 embedded inside the p-type semiconductor layer 42. The p-type semiconductor layer 42 is exposed to the first surface 21 of the semiconductor substrate 20, and constitutes a light receiving surface 44 on which light passing through the first filter layer 32 or the second filter layer 34 is incident.

The first photoelectric conversion unit 31 and the second photoelectric conversion unit 33 are embedded in a surface layer on the first surface 21 side of the semiconductor substrate 20. The light receiving surface 44 of the first photoelectric conversion unit 31 and the light receiving surface 44 of the second photoelectric conversion unit 33 are located on the same plane as the first surface 21 of the semiconductor substrate 20. The first filter layer 32 and the second filter layer 34 are located in the +Z direction with respect to the first surface 21.

The angle limiting filter layer 35 is formed at the first surface 21 of the semiconductor substrate 20 over an entire range in which the first photoelectric conversion unit 31 and the second photoelectric conversion unit 33 are disposed. The angle limiting filter layer 35 includes a first region 351 that overlaps the first photoelectric conversion unit 31, and a second region 352 that overlaps the second photoelectric conversion unit 33. In a layer of each of the first region 351 and the second region 352, a material having light-shielding properties and constituting an angle limiting filter 36 is disposed.

The first filter layer 32 has layer structure in which a band-pass filter layer 37 is stacked at a surface of the first region 351 in the angle limiting filter layer 35. The second filter layer 34 is formed only of the second region 352 of the angle limiting filter layer 35. In other words, the first light receiving unit 111 and the second light receiving unit 112 are different from each other in that the first light receiving unit 111 includes the band-pass filter layer 37, and the second light receiving unit 112 does not include the band-pass filter layer 37, and the other configurations are the same.

For example, the angle limiting filter layer 35 includes a conductive layer 51 made of a light reflective material such as an aluminum copper alloy (AlCu) alloy or titanium nitride (TIN), an interlayer insulating film 52 made of an optically transparent material such as silicon dioxide ($SiO_2$) or silicon nitride (SiN), and a light shielding body 53 formed inside the interlayer insulating film 52. The light shielding body 53 is, for example, a conductive plug formed of a light absorbing material such as tungsten (W). The angle limiting filter 36 includes the conductive layer 51 and the light shielding body 53 disposed so as to form an opening portion 54 overlapping the light receiving surface 44 formed by the p-type semiconductor layer 42, and the light shielding body 53 disposed in a columnar shape inside the opening portion 54.

The angle limiting filter 36, by the disposition of the above conductive layer 51 and the light shielding body 53, has a property of transmitting light incident at an angle smaller than a predetermined incident angle (hereinafter, referred to as an allowable incident angle) and blocking light incident at an angle larger than the allowable incident angle without transmitting the light. Accordingly, the first filter layer 32 limits an incident angle of light incident on the light receiving surface 44 of the first photoelectric conversion unit 31. Additionally, the second filter layer 34 limits an incident angle of light incident on the light receiving surface 44 of the second photoelectric conversion unit 33. Accordingly, the detection apparatus 3 can transmit light incident on the detection surface 10 of the detection apparatus 3 at the allowable incident angle after propagating the living body, and block light incident at an angle larger than the allowable incident angle, like outside light such as sunlight or light not incident on the living body.

A part of the conductive layer 51 and the light shielding body 53 (conductive plug) disposed at the angle limiting filter layer 35 constitutes wiring electrically coupled to the anode electrode 113 and the cathode electrode 114 of the first photoelectric conversion unit 31, and wiring electrically coupled to the anode electrode 115 and the cathode electrode 116 of the second photoelectric conversion unit 33.

The band-pass filter layer 37 includes, for example, a multilayer film 58 obtained by alternately stacking a thin film made of a low refractive index material such as silicon dioxide ($SiO_2$), and a thin film made of a high refractive index material such as titanium dioxide ($TiO_2$), and a light shielding wall 59 surrounding an outer periphery of the multilayer film 58. The light shielding wall 59 shields the second light LR (red light) and the third light LI (near-infrared light), for example. Note that, the light shielding wall 59 can be omitted. The multilayer film 58 has a property of selectively transmitting a wavelength band of the first light LG (green light) and absorbing and blocking the second light LR (red light) and the third light LI (near-infrared light) which are light of other wavelength bands.

Cross-Sectional Configuration of Light Emitting Unit

As illustrated in FIG. 4, the light emitting unit 12 includes the wiring layer 61 formed at the first surface 21 of the semiconductor substrate 20, an organic EL element forming unit 62 formed at a surface of the wiring layer 61, and a sealing layer 63 covering an entire range of the organic EL element forming unit 62 and a circumference thereof from the +Z direction. The sealing layer 63 is made of, for example, optically transparent inorganic material such as silicon dioxide ($SiO_2$) or silicon oxynitride (SiON). Note that, the sealing layer 63 may contain another material to an extent that sealing performance is not reduced. Further, the light emitting unit 12 includes a reflective layer 64 disposed inside a layer of the wiring layer 61. The reflective layer 64 is made of a light reflective material such as, for example, an aluminum copper alloy (AlCu).

Although not illustrated in FIG. 4, the wiring layer 61 extends up to an outer peripheral side of the sealing layer 63 at the first surface 21 of the semiconductor substrate 20. The terminals D1, D2, D3, and D4 (see FIG. 3) coupled to the light emitting unit 12 and the terminals C1, C2, C3, and C4 (see FIG. 3) coupled to the light receiving unit 11 are formed at the surface of the wiring layer 61 that extends to the outer peripheral side of the sealing layer 63.

The wiring layer 61 includes, for example, a conductive layer 55 made of a material such as an aluminum copper alloy (AlCu) or titanium nitride (TIN), an interlayer insulating film 56 made of optically transparent material such as silicon dioxide ($SiO_2$) silicon nitride (SiN), and a conductive plug 57 made of a material such as tungsten (W).

As illustrated in FIG. 4, each of a plurality of the interlayer insulating films 56 constituting the wiring layer 61 constitutes the same layer as the interlayer insulating film 52 constituting the angle limiting filter layer 35, and the interlayer insulating films 56 and 52 are formed to constitute a continuous layer. Further, the conductive layer 55 provided at the wiring layer 61 forms the same layer as the conductive layer 51 provided at the angle limiting filter layer 35. Accordingly, the angle limiting filter layer 35 and the wiring layer 61 may be formed at the semiconductor substrate 20 by the same process. Note that the layer configuration of the wiring layer 61 and the angle limiting filter layer 35 is not limited to the configuration illustrated in FIG. 4.

In the example illustrated in FIG. 4, positions and heights in the Z direction of the wiring layer 61 and the angle limiting filter layer 35 are substantially equal. The organic EL element forming unit 62 is formed at the surface of the wiring layer 61, and a height (thickness) in the Z direction of the organic EL element forming unit 62 is smaller than a height (thickness) in the Z direction of the band-pass filter layer 37. Accordingly, the first light emitting element 121, the second light emitting element 122, and the third light emitting element 123 as a whole are disposed within a range of a height in the Z direction of the first filter layer 32. That is, the first light emitting element 121, the second light emitting element 122, and the third light emitting element 123 are disposed at the same position as the first filter layer 32 in the Z direction. Note that, a magnitude relationship of height (thickness) in the Z direction between the band-pass filter layer 37 and the organic EL element forming unit 62 is not limited to the configuration illustrated in FIG. 4.

The organic EL element forming unit 62 includes a first light emitting region 621 constituting the first light emitting element 121, a second light emitting region 622 constituting the second light emitting element 122, and a third light emitting region 623 constituting the third light emitting element 123. Among the first light emitting region 621, the second light emitting region 622, and the third light emitting region 623, the first light emitting region 621 is disposed on a side closest to the light receiving unit 11, and the first light emitting region 621, the second light emitting region 622, and the third light emitting region 623 are aligned in this order toward a direction away from the light receiving unit 11.

The first light emitting region 621, the second light emitting region 622, and the third light emitting region 623 each include a first electrode 65 and a second electrode 66 facing in the Z direction, and an organic light emitting layer 67 formed between the first electrode 65 and the second electrode 66. The organic light emitting layer 67 contains an organic material that emits light by being supplied with current. The first light emitting region 621 includes a first light emitting layer 671 containing a green light emitting material as the organic light emitting layer 67. The second light emitting region 622 includes a second light emitting layer 672 containing a red light emitting material as the organic light emitting layer 67. The third light emitting region 623 includes a third light emitting layer 673 containing a near-infrared light emitting material as the organic light emitting layer 67. The first light emitting layer 671, the second light emitting layer 672, and the third light emitting layer 673 are disposed at the same layer.

Note that, the first light emitting region 621, the second light emitting region 622, and the third light emitting region 623 may each include a hole injection layer, a hole transport layer, an electron injection layer, and an electron transport layer, in addition to the organic light emitting layer 67, between the first electrode 65 and the second electrode 66.

The first light emitting element 121, the second light emitting element 122, and the third light emitting element 123 are top emission type organic EL elements capable of extracting light from the +Z side of the organic light emitting layer 67. The first light emitting element 121, the second light emitting element 122, and the third light emitting element 123 each include the reflective layer 64 disposed in a layer of the wiring layer 61. The reflective layer 64 is formed at a position overlapping from the −Z direction (that is, the semiconductor substrate 20 side) with each of the first light emitting layer 671, the second light emitting layer 672, and the third light emitting layer 673.

The first electrode 65 is an anode. The first electrode 65 is, for example, a transparent electrode made of indium tin oxide (ITO). The first electrode 65 is formed at a surface in the +Z direction of the wiring layer 61. In the present exemplary embodiment, the first electrode 65 is separated for each light emitting element. For example, the first electrodes 65 are formed at three locations respectively corresponding to the first light emitting region 621, the second light emitting region 622, and the third light emitting region 623

The second electrode 66 is a cathode. The second electrode 66 is, for example, an optically transparent electrode made of a silver magnesium alloy (AgMg). The second electrode 66 faces the organic light emitting layer 67 from a side opposite to the semiconductor substrate 20 (+Z direction). The second electrodes 66 of the three light emitting elements constitute one continuous electrode layer, and extend in a direction in which the first electrodes 65 at the three locations are aligned.

The conductive layer 55 and the conductive plug 57 are disposed at the wiring layer 61 so as to form wiring and anode contacts 126, 127, and 128 (see FIG. 3) for coupling each of the first electrodes 65 at the three locations to the drive circuit 13. Additionally, the conductive layer 55 and the conductive plug 57 are disposed at the wiring layer 61 so as to form wiring and a cathode contact 129 (see FIG. 3) for coupling the second electrode 66 to a GND of the drive circuit 13. The wiring structure inside the wiring layer 61, and the drive circuit 13 are configured to drive the first light emitting element 121, the second light emitting element 122, and the third light emitting element 123 by a passive matrix method.

The light receiving unit 11 and the light emitting unit 12 are covered by a cover plate 72 via a transparent resin layer 71. A surface in the +Z direction of the cover plate 72 constitutes the detection surface 10. The cover plate 72 has optical transparency, for example, and a glass plate or a quartz plate can be used. The transparent resin layer 71 is made of a transparent resin such as an epoxy resin or an acrylic resin, for example.

Main Effects of Present Exemplary Embodiment

As described above, the detection apparatus 3 of the present exemplary embodiment includes the semiconductor substrate 20, the first photoelectric conversion unit 31 formed at the semiconductor substrate 20, the first light emitting layer 671 formed by being stacked at the semiconductor substrate 20, and the first filter layer 32 formed by being stacked at the first photoelectric conversion unit 31.

More specifically, the detection apparatus 3 of the present exemplary embodiment includes the semiconductor substrate 20, the light emitting unit 12 formed at the first surface 21 of the semiconductor substrate 20, and the light receiving unit 11 formed at the position adjacent to the light emitting unit 12 at the first surface 21. The light receiving unit 11 includes the first photoelectric conversion unit 31 formed in the layer of the semiconductor substrate 20, and the first filter layer 32 formed at the surface of the first photoelectric conversion unit 31. The light emitting unit 12 includes the first light emitting element 121 disposed at the same position as the first filter layer 32 in the Z direction, which is a normal direction of the semiconductor substrate 20. The first light emitting element 121 includes the first electrode 65, the optically transparent second electrode 66 facing the first electrode 65 from the side opposite to the semiconductor substrate 20, and the first light emitting layer 671 formed between the first electrode 65 and the second electrode 66.

In the measuring apparatus 100 of the present exemplary embodiment includes the detection apparatus 3, and the control device 5 as the information analysis unit that identifies biological information from detection signals indicating detection results of the detection apparatus 3.

In the detection apparatus 3 of the present exemplary embodiment, the light receiving unit 11 and the light emitting unit 12 are formed with the common semiconductor substrate 20 as the base, and thus a gap (clearance) between the light receiving unit 11 and the light emitting unit 12 is smaller than that in the related art. As in the related art, when chipped LEDs and photodiodes are mounted at a substrate, a gap between the light receiving unit 11 and the light emitting unit 12 had a dimension in millimeters, but when the light receiving unit 11 and the light emitting unit 12 are formed by a technique of forming layer structure of a semiconductor layer, an insulator layer, a conductor layer constituting wiring, electrodes, and the like, an organic material layer, and the like, directly at the semiconductor substrate 20, a dimension of a gap between the first light emitting element 121 and the first light receiving unit 111 can be sized in microns. Accordingly, the size of the detection apparatus 3 can be reduced.

In addition, in the detection apparatus 3 of the present exemplary embodiment, in the light receiving unit 11, since the first photoelectric conversion unit 31 is formed in the layer of the semiconductor substrate 20, the height in the Z direction of the detection apparatus 3 is suppressed. In addition, in the light emitting unit 12, the entire organic EL element forming unit 62 that constitutes the first light emitting element 121 is disposed within the range of the height in the Z direction of the first filter layer 32. Accordingly, the detection apparatus 3 can be thinned.

When the gap between the light receiving unit 11 and the light emitting unit 12 can be reduced, an amount of light emitted from the light emitting unit 12 and returning from the measuring site M to the light receiving unit 11 increases. In particular, when the first light LG emitted from the light emitting unit 12 is the green light, the green light only diffuses to a shallow region in a body of the subject and returns, and thus an amount of received light suddenly decreases as a distance from the light emitting unit 12 increases. Accordingly, by reducing the gap between the light receiving unit 11 and the light emitting unit 12, the amount of received light of the first light LG (green light) emitted from the light emitting unit 12 can be increased. As a result, a required amount of light can be ensured even when an amount of emitted light of the first light emitting element 121 is reduced, and thus a power consumption of the light emitting unit 12 can be reduced. Accordingly, power saving of the detection apparatus 3 can be achieved. Furthermore, it is possible to receive more light that returns from the measuring site M, and thus an S/N ratio can be increased. As a result, the measuring apparatus 100 can identify biological information from the detection signal S having a high S/N, and thus can increase measurement accuracy.

Furthermore, the second electrode 66 is the optically transparent electrode, which is disposed on the side opposite to the semiconductor substrate 20, and is the top emission organic EL light emitting element, and thus the first light emitting element 121 emits a large amount of light. Accordingly, a required amount of light can be ensured even when an amount of electricity is lowered and an amount of emitted light is reduced, so the power consumption of the light emitting unit 12 can be reduced. Thus, power saving of the detection apparatus 3 can be achieved.

In the present exemplary embodiment, the light receiving unit 11 includes the second light receiving unit 112 including the second photoelectric conversion unit 33 formed in the layer of the semiconductor substrate 20, and the second filter layer 34 formed at the surface of the second photoelectric conversion unit 33. The second photoelectric conversion unit 33 is farther away from the light emitting unit 12 than the first photoelectric conversion unit 31. Further, the light emitting unit 12 includes the second light emitting element 122 that emits the second light LR (red light) having the wavelength larger than the first light LG (green light) emitted by the first light emitting element 121. The second light emitting element 122 is farther away from the first light receiving unit 111 than the first light emitting element 121.

Furthermore, the light emitting unit 12 includes the third light emitting element 123 that emits the third light LI (near-infrared light) having the wavelength larger than the second light LR. The third light emitting element 123 is farther away from the first light receiving unit 111 than the second light emitting element 122.

According to such a configuration, three types of light of the first light LG (green light), the second light LR (red light), and the third light LI (near-infrared light) can be emitted from the light emitting unit 12. Further, the light receiving unit 11 can receive light by the two photoelectric conversion units. Accordingly, since light in the plurality of wavelength bands can be received by the plurality of light receiving units, the detection signal S1 indicating the intensity of received light of the first light LG (green light), the detection signal S2 indicating the intensity of received light of the second light LR (red light), and the detection signal S3 indicating the intensity of received light of the third light LI (near-infrared light) can be acquired. In addition, various types of biological information can be identified from the detection signals S1, S2, and S3. For example, the pulse rate of the subject can be identified based on the detection signal S1. Furthermore, by analyzing the detection signal S2 and the detection signal S3, the oxygen saturation of the subject can be identified.

In the present exemplary embodiment, in the light emitting unit 12, the first light emitting element 121 that emits the first light LG (green light) is disposed closest to the light receiving unit 11. According to such a disposition, it is possible to cause the light receiving unit 11 to receive a large amount of the first light LG (green light) that propagates through the inside of the living body by a short distance and returns. Accordingly, even when intensity of emitted light of the first light emitting element 121 is suppressed, the first light LG (green light) propagating in the living body can be detected sufficiently in the light receiving unit 11. Thus, it is possible to increase an S/N ratio of the detection signal S1 indicating the intensity of received light of the first light LG (green light) while reducing the power consumption of the light emitting unit 12.

In the present exemplary embodiment, the first filter layer 32 provided at the first light receiving unit 111 includes the band-pass filter layer 37 that selectively transmits the light of the wavelength emitted from the first light emitting element 121 in the light emitting unit 12 (that is, the green light). As described above, the first light receiving unit 111 is disposed at the position closest to the light emitting unit 12 in the light receiving unit 11, and thus, receives a large amount of the first light LG (green light) that propagates by a short distance in the living body and then returns. Accordingly, by disposing the band-pass filter layer 37 at the first light receiving unit 111, the second light LR (red light) and the third light LI (near-infrared light) emitted from the other light emitting elements can be blocked to increase the S/N ratio of the detection signal S1 indicating the intensity of received light of the first light LG (green light). Furthermore, the band-pass filter layer 37 can block outside light in a wavelength band different from the green light, and thus noise due to the outside light can be reduced. Accordingly, the S/N ratio of the detection signal S1 indicating the intensity of received light of the first light LG (green light) can be increased.

In the present exemplary embodiment, the first filter layer 32 and the second filter layer 34 include the angle limiting filter layer 35. The angle limiting filter layer 35 transmits light incident at an angle smaller than the allowable incident angle and blocks light incident at an angle larger than the allowable incident angle. Accordingly, in each of the first light receiving unit 111 and the second light receiving unit 112, outside light incident from a direction different from the measuring site M of the living body can be blocked, and thus the S/N ratio of the detection signal S1 obtained from the first light receiving unit 111 can be increased, and S/N ratios of the detection signals S2 and S3 obtained from the second light receiving unit 112 can be increased.

Here, the second filter layer 34 does not include a band-pass filter layer. The first light LG (green light) can propagate only a short distance in the living body, compared to the second light LR (red light) or the third light LI (near-infrared light) as described above. Therefore, since the first light LG (green light) does not reach a position of the second light receiving unit 112, the first light LG (green light) does not enter the second photoelectric conversion unit 33 even without the band-pass filter layer. Thus, the band-pass filter layer can be omitted for the second light receiving unit 112, cost reduction can be achieved.

In the present exemplary embodiment, the light emitting unit 12 has the shape surrounding the light receiving unit 11, and in the light receiving unit 11, the first light receiving unit 111 has the shape surrounding the second light receiving unit 112. Thus, in the semiconductor substrate 20, the first photoelectric conversion unit 31 is formed in the shape surrounding the second photoelectric conversion unit 33. As described above, the first light LG (green light) propagates in the living body by a short distance and is emitted, and thus does not reach far, and a light amount that can be received is small. Accordingly, by configuring the light emitting unit 12 to surround the entire circumference of the light receiving unit 11, a light amount toward the light receiving unit 11 can be increased. In addition, by disposing the first photoelectric conversion unit 31 in a shape surrounding an entire circumference of the second photoelectric conversion unit 33, a configuration is obtained in which all of a region close to the light emitting unit 12 can receive the first light LG (green light). Accordingly, the mount of received light of the first light LG (green light) can be increased.

The light emitting unit 12 of the present exemplary embodiment includes organic EL element structure of a passive matrix type, without an active element such as a switching transistor being disposed for each light emitting element. Accordingly, since the structure of the light emitting unit 12 is simple, it is easy to manufacture the light emitting unit 12.

In the light emitting unit 12 of the present exemplary embodiment, the wiring layer 61 is provided with the reflective layer 64 at the position overlapping from the semiconductor substrate 20 side with each of the first light emitting layer 671, the second light emitting layer 672, and the third light emitting layer 673. Accordingly, in each light emitting element, light in a predetermined wavelength range of light generated by the organic light emitting layer 67 resonates between the reflective layer 64 and the second electrode 66 (cathode). Thus, a peak of wavelength distribution of light extracted from each light emitting element in the +Z direction becomes steep, and thus it is possible to increase intensity of the light (first light LG, second light LR, and third light LI) emitted from the light emitting unit 12, and increase color purity.

The detection apparatus 3 of the present exemplary embodiment includes the transparent cover plate 72 covering the light emitting unit 12 and the light receiving unit 11 from the side opposite to the semiconductor substrate 20, and the transparent resin layer 71 formed between the light emitting unit 12 and the light receiving unit 11 and the cover plate 72. As a result, a protective layer for protecting the light receiving unit 11 and the light emitting unit 12 can be formed. Additionally, the detection surface 10 can be configured by the cover plate 72.

Modified Example of Detection Apparatus (1) The light emitting unit 12 of the exemplary embodiment described above is configured to be capable of emitting light in the three wavelength bands of the first light LG (green light), the second light LR (red light), and the third light LI (near-infrared light), but any one of the third light emitting element 123 and the second light emitting element 122 may be omitted from the light emitting unit 12.

(2) In the exemplary embodiment described above, the first electrode 65 is the transparent electrode (ITO film), but the first electrode 65 may be a light-shielding electrode.

(3) In the exemplary embodiment described above, the light emitting unit 12 is configured to drive each light emitting element by the passive matrix method, but may be configured to drive each light emitting element by an active matrix method. For example, a switching transistor can be formed at a position overlapping in the Z direction with each light emitting element in a layer of the semiconductor substrate 20.

Figure 5:
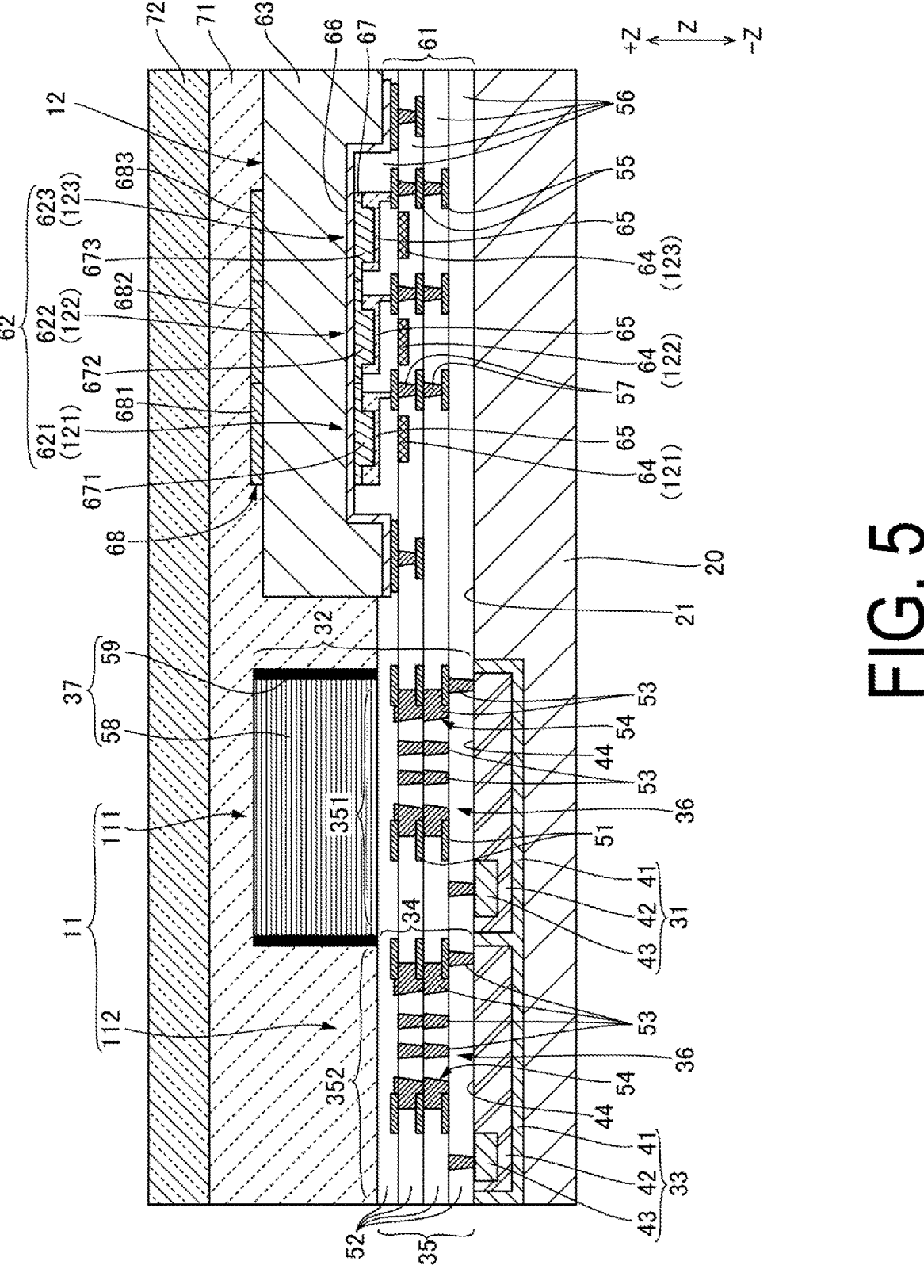
FIG. 5 is a cross-sectional view schematically illustrating a cross-sectional configuration of the light receiving unit and the light emitting unit when each light emitting element includes a color filter.

(4) The light emitting unit 12 may have a configuration in which each light emitting element includes a color filter. FIG. 5 is a cross-sectional view schematically illustrating a cross-sectional configuration of the light receiving unit 11 and the light emitting unit 12 when each light emitting element includes a color filter. As illustrated in FIG. 5, the first light emitting element 121 includes a first color filter 681 that overlaps the first light emitting layer 671. The second light emitting element 122 includes a second color filter 682 that overlaps the second light emitting layer 672. The third light emitting element 123 includes a third color filter 683 that overlaps the third light emitting layer 673. The first color filter 681, the second color filter 682, and the third color filter 683 are formed at a surface in the +Z direction of the sealing layer 63.

The first color filter 681 selectively transmits light in a wavelength band corresponding to the first light LG (green light). The second color filter 682 selectively transmits light in a wavelength band corresponding to the second light LR (red light). The third color filter 683 selectively transmits light in a wavelength band corresponding to the third light LI (near-infrared light). Since the first color filter 681, the second color filter 682, and the third color filter 683 are provided, color purity of the first light LG (green light), the second light LR (red light), and the third light LI (near-infrared light) emitted from the light emitting unit 12 can be increased.

(5) As illustrated in FIG. 5, when the configuration is adopted in which each light emitting element includes the color filter, any of the first light emitting layer 671, the second light emitting layer 672, and the third light emitting layer 673 can be formed of an organic material that emits white light.

(6) In the exemplary embodiment described above, both the first light receiving unit 111 and the second light receiving unit 112 include the angle limiting filter layer 35, but the angle limiting filter layer 35 may be omitted in one or both of the first light receiving unit 111 and the second light receiving unit 112. For example, when structure is adopted in which the light receiving unit 11 and the light emitting unit 12 can be shielded from outside light, the angle limiting filter layer 35 for reducing noise due to the outside light can be omitted.

Figure 6:
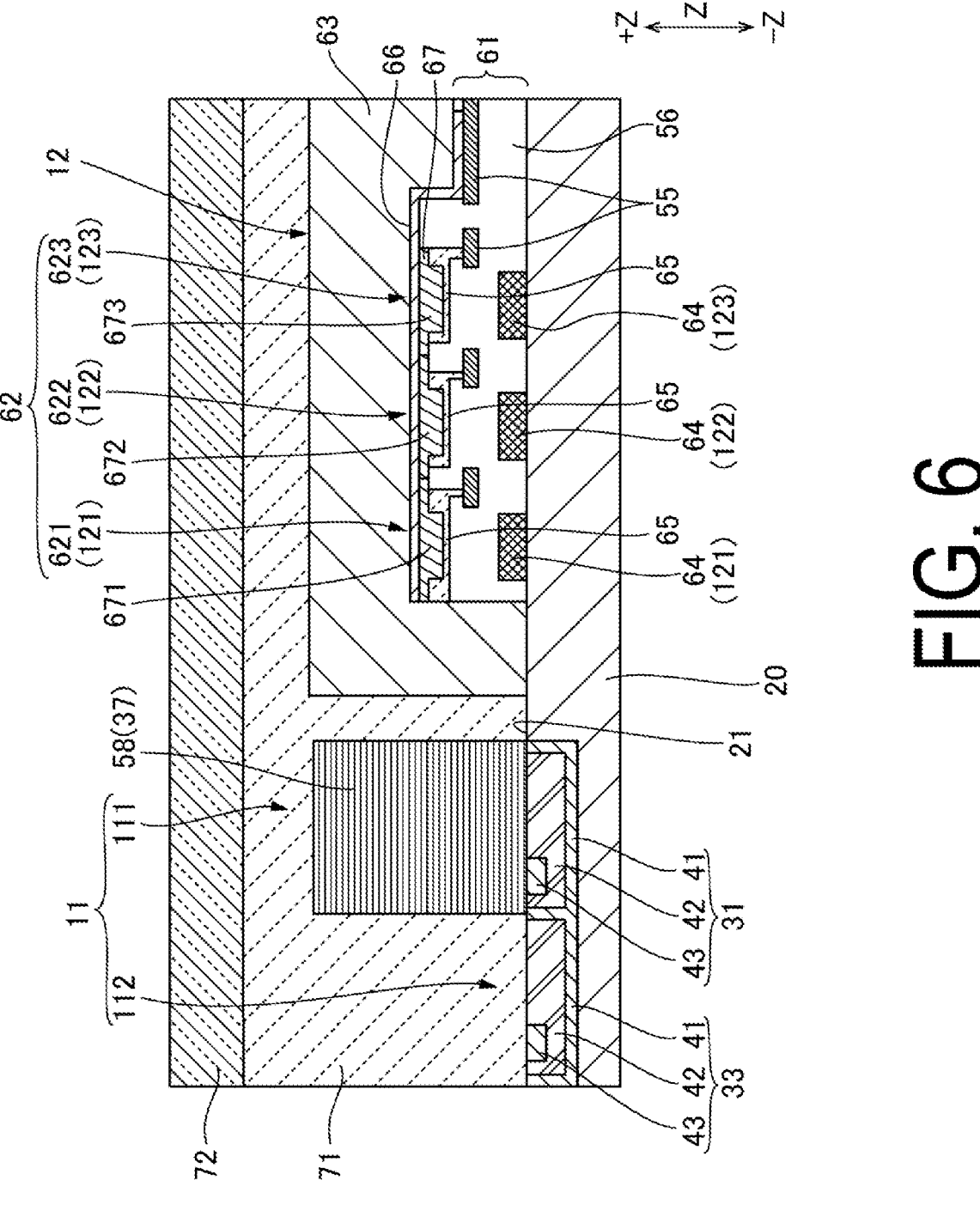
FIG. 6 is a cross-sectional view schematically illustrating a cross-sectional configuration of the light receiving unit and the light emitting unit when an angle limiting filter layer is omitted.

FIG. 6 is a cross-sectional view schematically illustrating a cross-sectional configuration of the light receiving unit 11 and the light emitting unit 12 when the angle limiting filter layer 35 is omitted. In the configuration illustrated in FIG. 6, the first light receiving unit 111 includes the first filter layer 32, and the first filter layer 32 only includes the band-pass filter layer 37. The second light receiving unit 112 does not include a filter layer, and the transparent resin layer 71 is formed at the surface of the second photoelectric conversion unit 33. The light emitting unit 12 includes the wiring layer 61, but the layer structure of the wiring layer 61 is simplified, as compared to the configuration illustrated in FIG. 4.

(7) In the exemplary embodiment described above, the second filter layer 34 does not include a band-pass filter layer, but the first filter layer 32 and the second filter layer 34 may be configured to include band-pass filter layers that pass light in different wavelength bands, respectively. For example, the second filter layer 34 can be provided with a band-pass filter layer that selectively transmits one or both of the second light LR (red light) and the third light LI (near-infrared light).

(8) In the exemplary embodiment described above, the entirety of the first light emitting element 121, the second light emitting element 122, and the third light emitting element 123 is disposed within the range of the thickness (height) in the Z direction of the first filter layer 32, but a configuration may be adopted in which a part or all in the Z direction of the first light emitting element 121, the second light emitting element 122, and the third light emitting element 123 are disposed outside the range of the thickness (height) in the Z direction of the first filter layer 32. For example, when the angle limiting filter layer 35 is omitted, as illustrated in FIG. 6, and a thickness (height) in the Z direction of the band-pass filter layer 37 is reduced, a part or all of the organic EL element forming unit 62 constituting the first light emitting element 121, the second light emitting element 122, and the third light emitting element 123 can be disposed in the +Z direction from the first filter layer 32.

Figure 7:
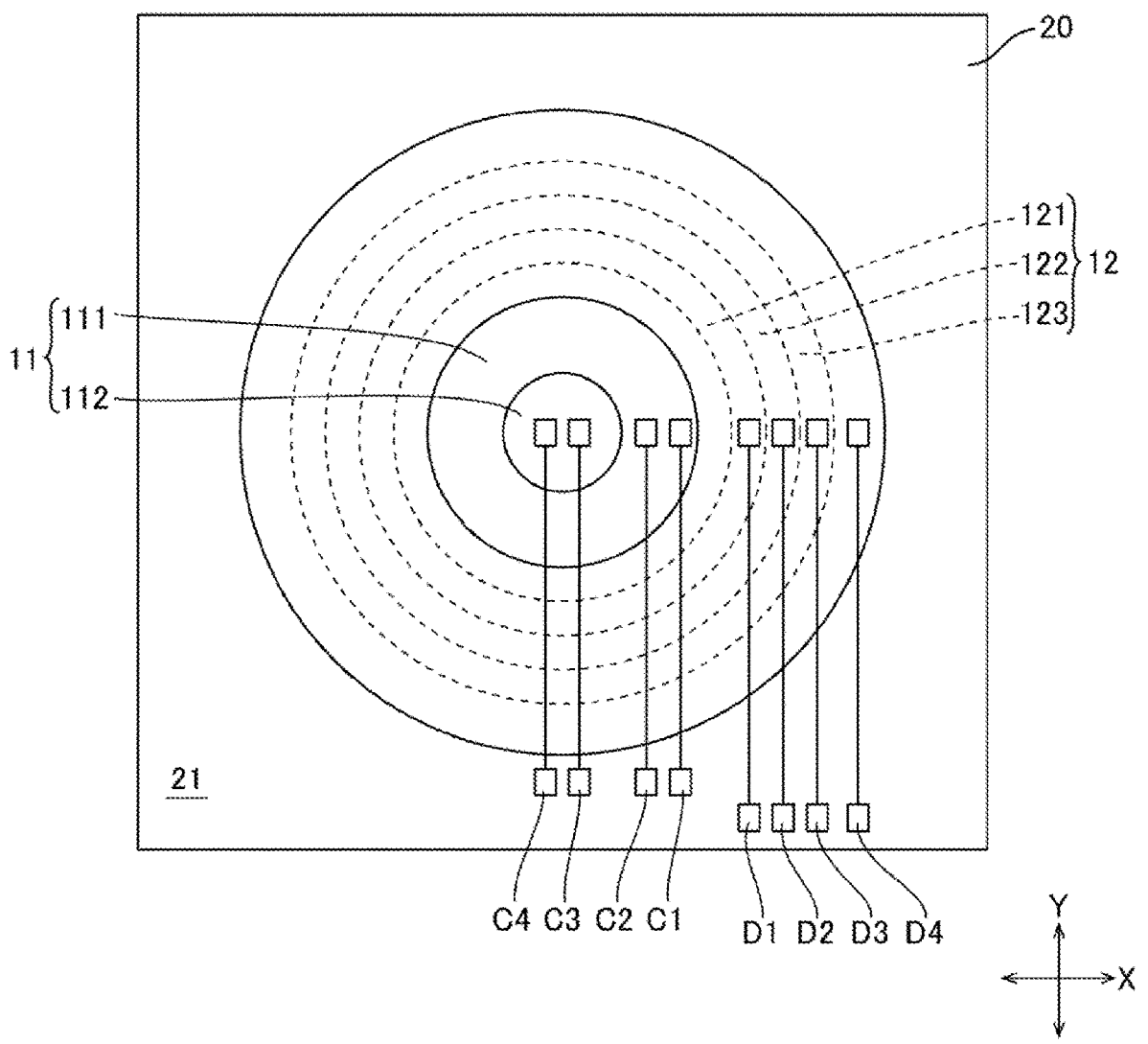
FIG. 7 is a plan view schematically illustrating planar shapes of a light receiving unit and a light emitting unit of a modified example.

(9) FIG. 7 is a plan view schematically illustrating planar shapes of the light receiving unit 11 and the light emitting unit 12 of the modified example. As illustrated in FIG. 7, for each of the light receiving unit 11 and the light emitting unit 12, a circular planar shape rather than a rectangular shape can be adopted.

What is claimed is:

1. A detection apparatus, comprising:

a semiconductor substrate;

a light emitter, which functions as a light emitting unit disposed at the semiconductor substrate, and configured to emit light toward a living body; and a light receiving unit disposed at the semiconductor substrate, and configured to receive the light from the living body, wherein the light receiving unit includes a first photoelectric conversion unit for receiving the light, and a first filter layer for limiting an incident angle of the light incident on the first photoelectric conversion unit, the light receiving unit is disposed at a position adjacent to the light emitting unit, the first filter layer is disposed at a surface of the first photoelectric conversion unit, the light emitting unit includes a first light emitting element, at least a part of which is disposed at a position identical to the first filter layer in a normal direction of the semiconductor substrate, and the first light emitting element includes a first electrode, an optically transparent second electrode, and a first light emitting layer disposed between the first electrode and the second electrode, and configured to emit the light.

2. The detection apparatus according to claim 1, wherein the first electrode has a light shielding property.

3. The detection apparatus according to claim 1, comprising a reflective layer at a position overlapping the first light emitting layer as viewed from the normal direction.

4. The detection apparatus according to claim 1, wherein the first filter layer includes a band-pass filter layer that selectively transmits a wavelength included in the light emitted from the first light emitting element.

5. The detection apparatus according to claim 4, wherein the light emitting unit includes a second light emitting element that emits second light having a wavelength longer than the first light emitted by the first light emitting element, and the second light emitting element is farther away from the light receiving unit than the first light emitting element is.

6. The detection apparatus according to claim 5, wherein the first light is light in a green wavelength band, the band-pass filter layer selectively transmits the first light, and the second light is light in a red wavelength band or a near-infrared wavelength band.

7. The detection apparatus according to claim 5, wherein the second light emitting element includes a second light emitting layer, the first light emitting element includes a first color filter that overlaps the first light emitting layer, and the second light emitting element includes a second color filter that overlaps the second light emitting layer.

8. The detection apparatus according to claim 5, wherein the light receiving unit includes a second photoelectric conversion unit formed in a layer of the semiconductor substrate, and a second filter layer formed at a surface of the second photoelectric conversion unit, and the second photoelectric conversion unit is farther away from the light emitting unit than the first photoelectric conversion unit is.

9. The detection apparatus according to claim 8, wherein each of the first filter layer and the second filter layer includes an angle limiting filter layer.

10. The detection apparatus according to claim 8, wherein when viewed from the normal direction, the light emitting unit has a shape surrounding the light receiving unit, and the first photoelectric conversion unit has a shape surrounding the second photoelectric conversion unit.

11. The detection apparatus according to claim 1, comprising:

a transparent cover plate configured to cover the light emitting unit and the light receiving unit from a side opposite to the semiconductor substrate; and a transparent resin layer formed between the light emitting unit and the light receiving unit, and the cover plate.

12. A measuring apparatus comprising:

the detection apparatus according to claim 1; and an information analysis unit configured to identify biological information from a detection signal indicating a detection result of the detection apparatus.

* * * * *